United States Patent [19]
Liao et al.

[11] Patent Number: 5,935,429
[45] Date of Patent: *Aug. 10, 1999

[54] CHROMATOGRAPHY COLUMNS WITH CONTINUOUS BEDS FORMED IN SITU FROM AQUEOUS SOLUTIONS

[75] Inventors: Jia-Li Liao, San Pablo, Calif.; Stellan Hjertén, Uppsala, Sweden

[73] Assignee: Bio-Rad Laboratories, Inc., Hercules, Calif.

[*] Notice: This patent is subject to a terminal disclaimer.

[21] Appl. No.: 08/964,768

[22] Filed: Nov. 5, 1997

Related U.S. Application Data

[63] Continuation-in-part of application No. 08/778,472, Jan. 3, 1997, abandoned.

[51] Int. Cl.$^6$ ................................................ B01D 15/08
[52] U.S. Cl. .................................. 210/198.2; 210/502.1; 210/635; 210/656
[58] Field of Search ................................. 210/656, 659, 210/198.2, 635, 198.3, 502.1; 422/70; 95/88; 96/101; 436/161

[56] References Cited

U.S. PATENT DOCUMENTS

| | | | |
|---|---|---|---|
| 3,298,925 | 1/1967 | Mosbach | 195/66 |
| 3,867,329 | 2/1975 | Halpern | 210/360.1 |
| 3,878,092 | 4/1975 | Fuller | 210/198.2 |
| 4,090,919 | 5/1978 | Chibata | 210/691 |
| 4,127,468 | 11/1978 | Alfenaar | 204/123 |
| 4,174,414 | 11/1979 | Sasaki | 156/254 |
| 4,201,766 | 5/1980 | Grollier | 424/70 |
| 4,340,483 | 7/1982 | Lucas | 210/198.2 |
| 4,352,884 | 10/1982 | Nakashima | 435/180 |
| 4,415,631 | 11/1983 | Schutijser | 210/198.2 |
| 4,474,663 | 10/1984 | Nakajima | 210/635 |
| 4,483,773 | 11/1984 | Yang | 55/386 |
| 4,565,832 | 1/1986 | Kobashi | 502/402 |
| 4,675,113 | 6/1987 | Graves | 210/198.2 |
| 4,743,373 | 5/1988 | Rai | 210/198.2 |
| 4,747,956 | 5/1988 | Kiniwa | 210/690 |
| 4,793,920 | 12/1988 | Cortes | 210/198.2 |
| 4,808,125 | 2/1989 | Good | 210/198.2 |
| 4,927,531 | 5/1990 | Sakamoto | 210/198.2 |
| 5,017,610 | 5/1991 | Hagen | 210/198.2 |
| 5,114,577 | 5/1992 | Kusano | 210/198.2 |
| 5,135,650 | 8/1992 | Hjerten | 210/198.2 |
| 5,159,049 | 10/1992 | Allen | 524/56 |
| 5,202,007 | 4/1993 | Kozulic | 204/182.8 |
| 5,306,404 | 4/1994 | Notsu | 204/182.8 |
| 5,334,310 | 8/1994 | Frechet | 210/198.2 |
| 5,645,717 | 7/1997 | Hjerten et al. | 210/198.2 |

FOREIGN PATENT DOCUMENTS

| | | | |
|---|---|---|---|
| 1 442 443 | 12/1969 | Germany | 210/198.2 |
| 6 803 739 | 6/1969 | Netherlands | 210/198.2 |
| WO 90/07965 | 7/1990 | WIPO | 210/198.2 |

OTHER PUBLICATIONS

Patent and Trademark Office Translation PTO91–4925 of Netherlands Patent Application 6803739, Oct. 1991, pp. 1–15.

Mikes Laboratory Handbook of Chromatographic and Allied Methods, John Wiley, New York, 1979, pp. 335,336, 343–347, & 412–414.

C. Ericson et al., *Journal of Chromatography A* (Apr. 11, 1997) 767 (1–2) : 33–41.

S. Hjerten et al., *Nature* (Apr. 30, 1992) 356: 810–811.

Y–M Li et al., *Analytical Biochemistry* (1994) 223: 153–158.

*Primary Examiner*—Ernest G. Therkorn
*Attorney, Agent, or Firm*—Townsend and Townsend and Crew LLP

[57] ABSTRACT

A chromatography column with a continuous solid bed spanning the cross section of the column, the bed containing channels large enough for hydrodynamic flow, is prepared by polymerizing a mixture of monomers and ammonium sulfate in an aqueous solution. The monomers include a monofunctional monomer such as a vinyl, allyl, acrylic, or methacrylic compound, and a polyfunctional monomer (i.e., a crosslinker), the total monomer concentration being in the range of 10% to 20% by weight, the mole ratio of crosslinker to total monomer being in the range of 0.3 to 0.4, and the ammonium sulfate having a concentration in the range of 0.4 M to 0.8 M. Functional groups to impart specialized separation capabilities, notably anion and cation exchange, can be included in the monomer mixture.

13 Claims, No Drawings

CHROMATOGRAPHY COLUMNS WITH CONTINUOUS BEDS FORMED IN SITU FROM AQUEOUS SOLUTIONS

CROSS REFERENCE TO RELATED APPLICATION

This application is a continuation-in-part of application Ser. No. 08/778,472, filed Jan. 3, 1997, now abandoned, the contents of which are incorporated herein by reference.

This invention relates to column chromatography using solid-phase separation media.

BACKGROUND OF THE INVENTION

Column chromatography is useful for both analytical and preparative separations, particularly for proteins and peptides. In analytical separations, the most efficient columns in many cases are high-performance liquid chromatography (HPLC), where a high back pressure (up to 6,000 psi) is applied to the column, and high resolution and reproducibility are sought. The binding capacity of the column is generally of little importance, and a high flow rate of sample through the column is generally used. Preparative separations are performed to extract purified proteins or peptides from a mixture rather than simply analyzing the mixture to determine its composition. While high resolution and reproducibility are still needed in preparative separations, the binding capacity and flow properties of the column are important as well, more so than in analytical columns. For preparative separations, therefore, it is important that high resolution be achieved with both a high binding capacity and a low back pressure (typically 1,000 psi or less).

High resolution requires both maximization of selectivity and minimization of band broadening. Factors that contribute to band broadening are longitudinal diffusion, eddy diffusion, and non-equilibrium mass transfer in both the mobile and stationary phases.

Longitudinal diffusion is of only minor concern for macromolecules. Eddy diffusion and non-equilibrium mass transfer in the mobile phase are of greater concern in packed beds, but both have been reduced by using columns packed with uniform particles with diameters in the 1- to 5-micron diameter range. Beds of this type, however, have high flow resistance. In addition, they are still susceptible to non-equilibrium mass transfer in the stationary phase, i.e., the diffusion of solute molecules into and out of the pores of the particles. This is a major contributing factor in band broadening, particularly with larger proteins due to their lower diffusion rates.

While diffusive mass transfer can be eliminated with the use of nonporous particles, the low surface area of such particles is detrimental to binding capacity. Surface area can be increased with the use of nonporous particles having diameters in the range of about 1 to 3 microns, but while the separations are rapid, particles of this size are not viable for preparative separations since they require a high back pressure. Another option is the use of perfusive particles, i.e., particles that contain both through-pores (6,000 to 8,000 Å) that traverse the particles and are large enough to accommodate hydrodynamic flow, and diffusive pores of a much smaller diameter (500 to 1,500 Å) that branch out from the through-pores. The through-pores however cause eddy diffusion, since the average linear velocity of mobile phase through a 7,000 Å through-pore in a 10 micron diameter particle is only 5% of the average linear velocity through the interstices between the particles, and the difference in flow rate is the cause of eddy diffusion. Furthermore, while the intraparticle convective flow reduces the time required for intraparticle solute transport, the slow diffusive transport of solutes in the small-diameter branch pores still dominates the solute flow. This causes band broadening at high flow rates.

Particles were avoided entirely by the introduction of a macroporous solid plug spanning the cross section of the column (Netherlands Patent Application No. 6,803,739, Czechoslovakian Academy of Sciences, Prague, laid open to public inspection Sep. 17, 1969). The macroporous plug eliminated the need to prepare particles and pack them into columns; the plug was instead prepared by polymerization in the column itself. By using an organic solvent as a porogen, however, the resulting plug was macroporous, i.e., with pores having diameters of approximately 0.1 microns or less. Pores of this size cause the diffusive transport discussed above, which impedes hydrodynamic flow and results in band broadening. Furthermore, the use of an organic solvent required that polymerization be performed under anhydrous conditions, and that the plug be extensively washed prior to performing separations that used an aqueous mobile phase. A still further disadvantage is that the resulting bed was hydrophobic, which would reduce its usefulness in most cases.

SUMMARY OF THE INVENTION

This invention resides in continuous beds formed in the column from an aqueous solution, without the use of a porogen, which term is used herein to denote any nonaqueous solvent or co-solvent that excludes the monomers as they are being polymerized. The bed is formed from a polymerization reaction mixture containing one or more water-soluble polymerizable compounds such as vinyl, allyl, acrylic and methacrylic compounds, and a crosslinking agent (both the polymerizable compound and the crosslinking agent are referred to collectively herein as "monomers"), and ammonium sulfate, in amounts such that:

(a) the sum of the weight percents of the monomers relative to the aqueous polymerization reaction mixture is within the range of about 10% to about 20%;

(b) the mole fraction of crosslinking agent relative to all monomers present in the polymerization reaction mixture is within the range of about 0.3 to about 0.4; and (c) the amount concentration of ammonium sulfate in the polymerization reaction mixture is within the range of about 0.4 to about 0.8 M. In (a) and (b), monomer that was present in the polymerization reaction mixture when first formed but did not react is not included in the calculation of these sums and mole fractions.

The continuous bed of this invention is a solid non-particulate separation medium that spans the cross section of the chromatography column. The bed has through-pores or channels that are large enough to permit hydrodynamic flow (i.e., having diameters generally of about 1 micron or greater), with substantially no pores of the macroporous range (about 0.1 microns or less). Most of the solute transport through the bed is therefore the result of hydrodynamic flow through the channels rather than diffusive flow through small-diameter branch pores. The channel walls themselves are substantially nonporous, although they have a rough surface, which contributes to the active surface area of the bed. The column itself is a tubular chromatographic column such as those used in HPLC and in capillary chromatography, and the continuous bed is formed directly in the column.

The monomers used to form the continuous beds of this invention can include charged monomers to form the bed as an ion exchange resin. The charged monomers are generally mixed with larger proportions of uncharged monomers. A further modification within the scope of the invention is the compression of the continuous bed subsequent to polymerization to increase the bed density and thereby the resolution of the solutes. With columns that are prepared for use as analytical columns, the degree of compression will be higher than in columns prepared as preparative columns.

These and other features and advantages of the invention are described and explained in detail below.

DETAILED DESCRIPTION OF THE INVENTION AND PREFERRED EMBODIMENTS

The monomers used in preparing the continuous beds of this invention include monofunctional monomers and polyfunctional monomers, the latter serving as crosslinking agents. The monomers and crosslinking agents may be charged or uncharged. The solubility of these species in water is preferably at least about 10%. Examples are vinyl, allyl, acrylic and methacrylic monomers. Preferred examples are vinyl acetate, vinyl propylamine, acrylic acid, butyl acrylate, acrylamide, methacrylamide, glycidyl methacrylate, glycidyl acrylate, methylene-bis-acrylamide, and piperazine diacrylamide.

When it is desired to derivatize the polymers by the attachment of functional groups, the monomers from which the polymers are formed may also contain reactive groups such as epoxide groups or hydroxyl groups to which covalent attachment is readily achieved. Monomers containing such groups are thus also within the scope of this invention. The monomers may be used singly or in combinations to vary the properties or qualities of the resulting polymer, including controlling the distribution and density of any functional groups present.

For ion exchange columns, it is preferred to include relatively small amounts of charged monomers with uncharged monomers. Charged monomers with conventional functional groups, whether positively or negatively charged, can be used. Examples of functional groups for anion exchangers are quaternary ammonium groups with either three or four alkyl substitutions on the nitrogen atom, the alkyl groups being primarily methyl or ethyl, and in some cases themselves substituted, for example with hydroxyl groups. Examples of functional groups for cation exchangers are sulfonic acid groups and carboxylic acid groups, joined either directly to the resin or through linkages. In each case, the strength of the ion exchanger is controlled by the substituents on the functional groups or by the combination of different functional groups, while the capacity of the exchanger is controlled by the number of functional groups (i.e., their concentration) per unit volume of the continuous bed.

As mentioned above, certain monofunctional monomers, particularly the charged monomers, will not fully react during the polymerization reaction, leaving much of the material in monomer form after the continuous bed is formed. The unreacted material is readily removed from the continuous bed product by washing the bed with water or a buffer solution. In these cases, a relatively high proportion of the monomer is included in the polymerization reaction mixture to compensate for the low degree of its inclusion in the resulting polymer. Regardless of whether all or only part of the monomer that is initially charged reacts, the mole ratio of charged monofunctional monomer to uncharged monofunctional monomer is not critical and can vary within the scope of this invention. Best results are generally achieved when the mole ratio of charged monofunctional monomer to uncharged monofunctional monomer is from about 0.01 to about 0.20, and preferably from about 0.05 to about 0.15. For anion exchange columns, preferred ratios of positively charged monofunctional monomer to uncharged monofunctional monomer are within the range of about 0.05 to about 0.10. For cation exchange columns, preferred ratios of negatively charged monofunctional monomer to uncharged monofunctional monomer are within the range of about 0.10 to about 0.15.

Crosslinking agents suitable for use in the present invention include any such bifunctional species capable of reacting with the monomer in a crosslinking manner. For polyacrylamides and polymers of other forms of acrylic acid, examples of suitable crosslinking agents are bisacrylamides, diacrylates, and a wide range of terminal dienes. Specific examples are dihydroxyethylenebisacrylamide, diallyltartardiamide, triallyl citric triamide, ethylene diacrylate, bisacrylylcystamine, N,N'-methylenebisacrylamide and piperazine diacrylamide. The latter two are preferred, and piperazine diacrylamide is particularly preferred.

The quantity of monomer and the proportion of crosslinking agent are conveniently characterized by two parameters, one representing the total monomer concentration (both monofunctional and polyfunctional) in the polymerization solution (but excluding any monomers that remain unreacted and are thereafter removed from the solid continuous bed by washing), and the other representing the proportion of crosslinking agent relative to total monomer. The first is conveniently expressed as a weight percent or a weight/volume percent (which is numerically very close to a weight percent), defined as milligrams of monomer plus crosslinking agent per milliliters of solution, multiplied by 0.1, and is represented herein by the symbol "T". The second is conveniently expressed as a weight/weight percent, defined as milligrams of crosslinking agent divided by milligrams of crosslinking agent plus monomer, multiplied by 100, and is represented herein by the symbol "C". For monomers and crosslinking agents expressed generically, the weight/volume percent "C" is replaced by the mole fraction of crosslinking agent relative to the total of monomer plus crosslinking agent.

In accordance with the present invention, the value of T ranges from about 10% to about 20%, and preferably from about 12.5% to about 17%. Likewise, the value of C ranges from about 0.3 to about 0.4, preferably from about 0.32 to about 0.36.

One of the components of the polymerization reaction mixture that contributes significantly to the qualities of the polymer is the ammonium sulfate. A suitable range of ammonium sulfate concentration for this invention is about 0.4 M (0.8 N) to about 0.8 M (1.6 N) (moles, or in parentheses equivalents, of ammonium sulfate per liter of the entire solution). A preferred range is about 0.5 M (1.0 N) to about 0.7 M (1.4 N).

To form the polymer directly in the column in which it will be used for chromatography, conventional polymerization techniques well known among those skilled in the art may be used. The aqueous monomer solution will generally also contain one or more polymerization catalysts and other conventional additives, and polymerization is permitted to proceed directly in the casing or column tube in which the medium will be used. For microcolumns with inside diameters less than or equal to about 2 mm, it will be advantageous to covalently bind the medium to the inner wall of the column. This may be achieved by binding agents, such as for example vinyl propyl trichlorosilane, according to conventional techniques.

The performance of the polymer as a chromatographic separation medium is in many cases enhanced by forcible compression of the bed subsequent to its formation. Beds to be compressed are preferably not covalently linked to the wall of the column tube. A possible reason for this improvement is the shortening of the flow path between neighboring polymer particles or channel walls, and hence an increase in the interaction between the solutes and the polymer surface as the sample being separated passes through the bed. Compression may be achieved by the simple application of force, as by a plunger inserted into the column at the end opposite the water-permeable retaining member referred to above, or by the passage of water through the column at a high flow rate, or by any of various other means which will readily occur to those skilled in the art. Compression will usually be done to less than about 75% of the original volume of the polymer, and preferably to about 25% to about 70% of the original polymer volume. In many applications, compression by a factor of at least 5 (i.e., to about one-fifth of the noncompressed volume), and even by a factor of about 10 to about 15, is desirable. For preparative chromatography columns, compression is preferably limited to an amount within the range of about 10% to about 30% (i.e., reduction of the bed volume by a percent within this range), while for analytical chromatography columns, a greater degree of compression is preferred, such as an amount within the range of about 30% to about 70%.

The continuous bed polymer may be chemically modified to provide it with a selected chromatographic character as appropriate for particular types of separations. Functional groups may be copolymerized into the structure initially, or the surface of the polymer, once formed, may be chemically modified. For example, non-polar ligands may be covalently attached to the polymer to improve its effectiveness as a medium for reversed-phase chromatography. Examples of nonpolar ligands are long-chain saturated aliphatic groups such as linear chains of 6 or more carbon atoms. Ligands of 8 to 18 carbon atoms are particularly useful in this regard. Covalent attachment may be achieved through conventional linkages at the polymer surface, using functional groups on monomers forming the polymer backbone or on secondary monomers incorporated into the backbone as described above. The polymer may likewise be rendered suitable for cation or anion exchange chromatography by the covalent attachment of appropriately charged functional groups to the polymer backbone, by the conversion of groups already on the backbone to charged moieties, or by copolymerization with monomers that contain charged functional groups, as indicated above. A still further treatment of the polymer is the coating of the polymer with hydrophilic species by covalent attachment, to reduce nonspecific interaction. The coated polymer may then be derivatized as desired to achieve a specific type of interaction. When used in a chromatographic separation, the resulting polymer offers greater resolution. Coating of the polymer with hydrophilic species may further be used as a means of providing more coupling sites for derivatization, by selecting a coating with a high density of functional groups available for coupling, or as a means of avoiding non-specific hydrophobic interaction.

Once prepared by any of the techniques described above, the separation medium of the present invention may be used for a wide variety of separations, including peptides, proteins, and other types of mixtures in biological or other samples. The mobile phase is an aqueous phase, preferably a buffer solution with a pH of about 1.0 to about 13.0, and flow is achieved either by pumping or by gravity flow. For cation exchange columns, a preferred range for the mobile phase pH is about 6.0 to about 7.0. For anion exchange columns, a preferred range for the mobile phase pH is about 7.5 to about 9.0. For reverse-phase columns, a preferred range for the mobile phase pH is about 2.0 to about 5.0, with a mobile phase with pH 2 being commonly used. Detection of the eluting solutes is readily achieved by conventional means, either in the column itself, using staining methods if necessary, or outside the column at the downstream end. Separation media of this type are particularly effective for the separation of species having molecular weights ranging from about 100 to about 1,000,000, and most notably about 1,000 to about 1,000,000.

The following examples are offered for purposes of illustration, and are intended neither to limit nor to define the invention in any manner.

EXAMPLES

The following are examples of polymerization reaction mixtures for continuous beds in accordance with this invention, designed for various uses, as indicated.

Table I lists the components used in the formation of an anion-exchange column system used for preparative chromatography to purify biomolecules. The column system consists of a primary glass column followed by a PEEK (polyetherketone) polisher column.

TABLE I

Illustrative Anion Exchange Column for Preparative Chromatography

|  | Primary Column (glass) | Polishing Column (PEEK) |
|---|---|---|
| Dimensions: | | |
| internal column diameter | 7 mm, 12 mm, or 15 mm | 4.6 mm |
| final bed volume | 1.3 mL, 6.0 mL or 12.0 mL | 0.16 mL |
| Composition of Polymerization Reaction Mixture: | | |
| 0.1 M Sodium Phosphate, pH 7.0 | 3.0 mL | 2.5 mL |
| Diallyl Dimethyl Ammonium Chloride, 65 weight %, polymerization rate 5.62% | 1.0 mL 1.9 mL | |
| Methacrylamide | 264 mg | 264 mg |
| Piperazine Diacrylamide | 336 mg | 336 mg |
| Ammonium Sulfate | 420 mg | 420 mg |
| Ammonium Persulfate, 10% (weight/volume) | 100 μL | 200 μL |
| N,N,N',N'-tetramethylethylenediamine | 100 μL | 200 μL |
| T value (weight %) | 12.6% | 13.4% |
| C value (mole ratio) | 0.36 | 0.36 |
| $(NH_4)_2SO_4$ concentration (N) | 1.33 | 1.41 |
| Bed volume reduction due to post-polymerization compression | 60% | 60% |

Table II lists the components used in the formation of a cation-exchange column system used for preparative chromatography to purify biomolecules, using the same column system as Table I.

TABLE II

Illustrative Cation Exchange Column for Preparative Chromatography

| | Primary Column (glass) | Polishing Column (PEEK) |
|---|---|---|
| Dimensions: | | |
| internal column diameter | 7 mm, 12 mm, or 15 mm | 4.6 mm |
| final bed volume | 1.3 mL, 6.0 mL or 12.0 mL | 0.16 mL |
| Composition of Polymerization Reaction Mixture: | | |
| 0.1 M Sodium Phosphate, pH 7.0 | 4.0 mL | 3.5 mL |
| 2-Acrylamido-2-methyl-1-propanesulfonic acid, polymerization rate 100% | 80 mg | 80 mg |
| NaOH, 5.0 N | 80 µL | 80 µL |
| Methacrylamide | 264 mg | 264 mg |
| Piperazine Diacrylamide | 336 mg | 336 mg |
| Ammonium Sulfate | 340 mg | 420 mg |
| Ammonium Persulfate, 10% (weight/volume) | 80 µL | 80 µL |
| N,N,N',N'-tetramethylethylene diamine | 80 µL | 80 µL |
| T value (weight %) | 13.6% | 15.1% |
| C value (mole ratio) | 0.36 | 0.36 |
| $(NH_4)_2SO_4$ concentration (N) | 1.0 | 1.4 |
| Bed volume reduction due to post-polymerization compression | 60% | 60% |

The mixtures listed in Tables I and II can also be scaled up to form bed volumes of 10 mL to 100 mL and beyond, and to be run at flow rates up to 100 mL/min and back pressures up to 1,500 psi. The continuous beds formed from the mixtures listed in Tables I and II are preferably compressed prior to use. Compression by about 60% of the bed volume results in a column that is particularly useful for medium-pressure preparative chromatography, while compression by about 10%–30% (preferably about 20%) of the bed volume results in a column that is particularly useful for low-pressure preparative chromatography.

Tables III and IV list materials that can be used for anion and cation exchange columns, respectively, designed for high-pressure analytical chromatography, with back pressures of up to 3,000 psi.

TABLE III

Illustrative Anion Exchange Column for High-Pressure Analytical Chromatography

| Dimensions: | |
|---|---|
| internal column diameter | 4.6 mm |
| final bed volume | about 1 mL |
| Composition of Polymerization Reaction Mixture: | |
| 0.1 M Sodium Phosphate, pH 7.0 | 2.5 mL |
| Diallyl Dimethyl Ammonium Chloride, 65 weight %, polymerization rate 5.62% | 1.2 mL |
| Methacrylamide | 264 mg |
| Piperazine Diacrylamide | 336 mg |
| Ammonium Sulfate | 350 mg |
| Ammonium Persulfate, 10% (weight/volume) | 100 µL |
| N,N,N',N'-tetramethylethylene-diamine | 100 µL |
| T value (weight %) | 14.3% |
| C value (mole ratio) | 0.34 |
| $(NH_4)_2SO_4$ concentration (N) | 1.18 |
| Bed volume reduction due to post-polymerization compression | 50% |

TABLE IV

Illustrative Cation Exchange Column for High-Pressure Analytical Chromatography

| Dimensions: | |
|---|---|
| internal column diameter | 4.6 mm |
| final bed volume | about 1 mL |
| Composition of Polymerization Reaction Mixture: | |
| 0.1 M Sodium Phosphate, pH 7.0 | 3.5 mL |
| 2-Acrylamido-2-methyl-1-propane-sulfonic acid, polymerization rate 100% | 120 mg |
| NaOH, 5.0 N | 120 µL |
| Methacrylamide | 264 mg |
| Piperazine Diacrylamide | 336 mg |
| Ammonium Sulfate | 340 mg |
| Ammonium Persulfate, 10% (weight/volume) | 80 µL |
| N,N,N',N'-tetramethylethylene-diamine | 80 µL |
| T value (weight %) | 16% |
| C value (mole ratio) | 0.32 |
| $(NH_4)_2SO_4$ concentration (N) | 1.14 |
| Bed volume reduction due to post-polymerization compression | 50% |

The foregoing is offered primarily for purposes of illustration. It will be readily apparent to those skilled in the art that modifications and substitutions in terms of the materials, procedures and other parameters of the system may be introduced without departing from the spirit and scope of the invention.

We claim:

1. A chromatography column having an internal cross section spanned by a continuous solid non-particulate separation medium, said separation medium formed by polymerization of a monomer mixture comprising:
   (a) a water-soluble polymerizable compound selected from the group consisting of vinyl, allyl, acrylic and methacrylic compounds, and
   (b) a crosslinking agent, in an aqueous solution that further contains
   (c) ammonium sulfate,
   whereby the sum of the weight percents of monomers in said monomer mixture relative to said aqueous solution is from about 10% to about 20%, the mole fraction of said crosslinking agent relative to the sum of monomers in said monomer mixture is from about 0.3 to about 0.4, and the concentration of ammonium sulfate in said aqueous solution is from about 0.4 to about 0.8 moles per liter.

2. A chromatography column in accordance with claim 1 in which (a) is a mixture comprising
   (i) a member selected from the group consisting of vinyl acetate, acrylic acid, butyl acrylate, acrylamide, methacrylamide, and glycidyl acrylamide, and
   (ii) a member selected from the group consisting of vinyl, acrylic and methacrylic monomers to which charged groups are covalently attached.

3. A chromatography column in accordance with claim 2 in which (ii) is a member selected from the group consisting of vinyl, allyl, acrylic and methacrylic monomers to which positively charged groups are covalently attached, and the concentration of ammonium sulfate in said aqueous solution is from about 0.5 to about 0.7 moles per liter.

4. A chromatography column in accordance with claim 2 in which (i) is methacrylamide.

5. A chromatography column in accordance with claim 2 in which (i) is methacrylamide and (b) is piperazine diacrylamide.

6. A chromatography column in accordance with claim 2 in which the mole ratio of (ii) to (i) is from about 0.01 to about 0.20.

7. A chromatography column in accordance with claim 2 in which the mole ratio of (ii) to (i) is from about 0.05 to about 0.15.

8. A chromatography column in accordance with claim 2 in which (i) is methacrylamide and (ii) is diallyl dimethyl ammonium chloride, and the mole ratio of (ii) to (i) is from about 0.05 to about 0.10.

9. A chromatography column in accordance with claim 2 in which (i) is methacrylamide and (ii) is 2-acrylamido-2-methyl-1-propanesulfonic acid, and the mole ratio of (ii) to (i) is from about 0.10 to about 0.15.

10. A chromatography column in accordance with claim 1 in which (b) is a member selected from the group consisting of N,N'-methylene-bis-acrylamide and piperazine diacrylamide.

11. A chromatography column in accordance with claim 1 in which (b) is piperazine diacrylamide.

12. A chromatography column in accordance with claim 1 in which the sum of the weight percents of monomers in said monomer mixture relative to said aqueous solution is from about 12.5% to about 17%.

13. A chromatography column in accordance with claim 1 in which the mole fraction of said crosslinking agent relative to the sum of monomers in said monomer mixture is from about 0.32 to about 0.36.

* * * * *